United States Patent [19]

De Thomas

[11] Patent Number: 4,851,085

[45] Date of Patent: Jul. 25, 1989

[54] PURIFICATION OF BUTYROLACTONE

[75] Inventor: Waldo De Thomas, Parsippany, N.J.

[73] Assignee: GAF Corporation, Wayne, N.J.

[21] Appl. No.: 217,511

[22] Filed: Jul. 11, 1988

[51] Int. Cl.$^4$ .................. B01D 3/06; B01D 3/10; C07D 307/32

[52] U.S. Cl. ........................................ 203/35; 203/38; 203/88; 203/91; 203/DIG. 6; 549/295

[58] Field of Search ................. 203/6, DIG. 6, 34, 35, 203/61, 88, 91, 38; 549/295

[56] References Cited

U.S. PATENT DOCUMENTS

| | | | |
|---|---|---|---|
| 2,229,532 | 1/1941 | Vanderbilt | 203/30 |
| 2,429,484 | 10/1947 | Peters | 203/30 |
| 2,875,213 | 2/1959 | Ulvild et al. | 549/295 |
| 2,955,133 | 10/1960 | Hort | 549/295 |
| 3,037,052 | 5/1962 | Bortnick | 549/295 |
| 3,530,149 | 9/1970 | Fiecchi | 549/295 |
| 3,786,069 | 1/1974 | Violet et al. | 549/295 |
| 4,309,352 | 1/1982 | Ho | 549/295 |
| 4,384,114 | 5/1983 | Jautelat | 549/322 |
| 4,391,981 | 7/1983 | Brois et al. | 549/252 |
| 4,596,879 | 6/1986 | Fizet | 549/295 |
| 4,707,491 | 11/1987 | Covey et al. | 549/62 |
| 4,767,869 | 8/1988 | Harrison et al. | 203/60 |

Primary Examiner—Virginia Manoharan
Attorney, Agent, or Firm—Marilyn J. Maue; Joshua J. Ward

[57] ABSTRACT

A process which comprises treating butyrolactone in at least 95% purity with an acid to convert and remove color forming impurities for product stabilization.

11 Claims, No Drawings

PURIFICATION OF BUTYROLACTONE

BACKGROUND OF THE INVENTION

Butyrolactone is a chemical having wide application and is conventionally used as a solvent for polymers, fluorinated hydrocarbons, shellac and cellulose triacetate. Its solvent properties also make it useful in paint removers, petroleum processing and in the selective extraction of water immiscible alcohols. The compound also finds application as a chemical intermediate for monoazo dye stuffs and as an agricultural chemical adjuvant in herbicidal, fungidical, insecticidal and plant growth regulator formulations.

Generally, butyrolactone is produced by various processes involving high pressure synthesis from acetylene and formaldehyde. These processes are capable of producing a substantially pure product which is further purified by subjecting the crude product to fractional distillation. However, it has been found that butyrolactone purified by distillation through a fractionating column is not color stable on standing at ambient temperature and undergoes significant coloration at temperatures above about 20° C. Also, in acid formulations, butyrolactone develops an objectionable dark color which inhibits its use in certain dyestuffs and photosensitive emollients. Various processes have been proposed to reduce product degradation including expensive and time consuming extractions, multiple washings, etc.

Accordingly it is an object of this invention to provide an economical and commercially feasible butyrolactone purification process which maximizes color stability at ambient and elevated temperatures in acid or basic media.

THE INVENTION

In accordance with the present invention, a butyrolactone feed of at least 95% purity is subjected to treatment with a strong acid, preferably a strong mineral acid such as sulfuric, phosphonic, nitric, or hydrochloric acids or a strong acid ion exchange resin, by agitation at a temperature between about 25° C. to about 200° C. for a period of from about 1 to about 48 hours, preferably from about 3 to about 24 hours. The amount of acid employed can vary between about 0.05 and about 3 wt. %, preferably between about 0.1 and about 1 wt. % acid, based on butyrolactone. After the acid treatment is complete, the resulting mixture is subjected to vacuum distillation under from about 1 to about 200 mm Hg at a temperature of between about 90° C. and about 180° C., preferably under from about 50 to about 100 mm Hg at a temperature of between about 125° C. and about 135° C. The color forming and high boiling components are thus removed and the product is collected in a purity of at least 99%. This product is color stable at ambient and elevated temperatures in both acid or basic media.

The acid treatment of the present invention converts the color forming impurities, which include aldehydes, ketones, and unsaturated compounds, generally present in only trace amounts, by polymerization or conversion to a non-color forming products which remain in the residue during vacuum distillation. The treatment also removes trace metal ions such as Na, K, Ca and Fe which is beneficial for electronics and pharmaceutical applications.

Although strong mineral or ion exchange acids are preferred in the above treatment, certain organic acids may also be employed to effect polymerization of color formers. These acids include high boiling carboxylic acid, preferably polyacids such as succinic, citric, tartaric, suberic, oleic, lauric, citraconic and aconitric acids. The strong acid ion exchange resins which include sulfonic or phosphonic acids as well as cross linked resin solids of the strong acid type, such as the strong acid AMBERLYSTS and AMBERLITES are also usefully employed.

When acids in particulate solid form are used, the particles can be disposed in a column as a fixed bed and the lactone passed through the bed at a rate of between about 10 ml and about 40 ml/hr. in a continuous operation. Examples of particulate strong acid ion exchange resins include AMBERLYST 15, AMBERLYST XN-1010 and AMBERLITE IR-120 and others of these types.

Having thus generally described the invention reference is now had to the accompanying examples which set forth preferred embodiments; however it is to be understood that these examples do not limit the scope of the invention as described above and in the appended claims.

EXAMPLE 1

Into a 250 cc round bottom glass flask was charged 99.8 grams of distilled grade butyrolactone of about 98% purity and 0.2 grams of concentrated sulfuric acid. This mixture was stirred to assure good mixture and then heated under nitrogen at 175° C. for 4 hours. The reaction mixture was then flashed distilled through a single plate column at 1 mm Hg vacuum and a maximum pot temperature of 94° C. The distillate was collected and was found to have a Hardy color of APHA 45. Testing of the same butyrolactone sample after flash distillation without the acid treatment (the control standard) was found to have a Hardy color of APHA 2090. The thermal color stability of the acid treated butyrolactone and the control, after 4 hours at a 100° C. under nitrogen was found to be APHA 22 for the acid treated product as compared to APHA 96 for the control.

EXAMPLE 2

Example 1 was repeated except that 99.75 grams of butyrolactone having a purity of about 97% and 0.25 grams of concentrated sulfuric acid was introduced into the round bottom glass flask. This mixture was agitated and heated to 98° C. for 5 hours followed by the flash distillation described in Example 1. This product had a Hardy color of APHA 1 as compared with its control standard having an APHA 85. The thermal color stability of the acid treated butyrolactone at a 100° C. for 4 hours under nitrogen was APHA 3 versus the control standard at APHA 73.

EXAMPLE 3

Example 1 was repeated except that the acid butyrolactone mixture was heated at a 100° C. for 30 minutes and then flashed distilled. The Hardy color of the acid treated product was APHA 84 compared to the control standard at APHA 3040.

EXAMPLE 4

Into a 250 cc round bottom glass flask was charged 99.6 grams of distillate grade butyrolactone and 0.4 grams of concentrated sulfuric acid. This mixture was stirred and allowed to stand 16 hours at ambient temperature under nitrogen. The solution was then flashed distilled through a single plate column at 1.5 mm Hg vacuum and a maximum pot temperature of 92° C. The product had a Hardy color of APHA 44 versus a flash distilled control standard omitting the acid treatment which had a Hardy color of APHA 3040.

EXAMPLE 5

Example 1 was repeated except that phosphoric acid was substituted for sulfuric acid. The acid treated butyrolactone had a Hardy color of APHA 55 versus the distilled control standard omitting acid treatment of APHA 2200.

EXAMPLE 6

A 25 cc burette was filled with distilled grade butyrolactone and 10 cc of AMBERLYST 15, a strong acid resin, was added forming a packed bed. The bed was heated to 80° C. and butyrolactone was passed through the resin at a rate of 20 ml per hour. The treated butyrolactone was collected and flashed distilled at 80 mm Hg vacuum and a maximum pot temperature of 135° C. The fraction from this distillation had a Hardy color of APHA 42, as compared with the flash distilled control standard of APHA 445.

EXAMPLE 7

Example 6 was repeated except that AMBERLYST XN-1010 strong acid resin was substituted for AMBERLYST 15. The acid treated, flashed distilled butyrolactone had a Hardy color of APHA 240 as compared with the flashed distilled control standard omitting acid treatment of APHA 710.

Many alterations and variations in the above described process are within the scope of this invention and will become apparent to those skilled in the art. For example, the above acid treatment can be employed to convert and remove trace quantities of color forming impurities from other substantially pure lactone feed stocks such as a valerolactone, propiolactone and others.

What is claimed is:

1. A process for producing a color stable butyrolactone product, said process comprises contacting butyrolactone having a purity of at least 95% with between about 0.05 and about 3 weight % of a strong acid at a temperature of from about 25° C. to about 200° C. for a period of from about 1 hour to about 48 hours and then vacuum distilling the resulting mixture at a temperature between about 90° C. and about 180° C. under a pressure from about 1 to about 200 mm Hg such that color forming impurities of said butyrolactone are removed and a color stable butyrolactone product of improved purity is produced.

2. The process of claim 1 wherein said acid is a strong mineral acid.

3. The process of claim 2 wherein said mineral acid is concentrated sulfuric acid.

4. The process of claim 2 wherein said mineral acid is concentrated phosphoric acid.

5. The process of claim 1 wherein said acid is a strong ion exchange resin acid.

6. The process of claim 1 wherein said acid is a polycarboxylic acid.

7. The process of claim 1 wherein said butyrolactone is contacted with between about 0.1 and about 1 weight % of said acid.

8. The process of claim 7 wherein the vacuum distillation is effected under from about 50 to about 100 mm Hg at a temperature of between about 125° C. and about 135° C.

9. The process of claim 7 wherein said acid is a strong mineral acid and the butyrolactone is contacted with said acid for a period of from about 3 to about 24 hours.

10. The process of claim 7 wherein said acid is a particulate strong acid ion exchange resin disposed in a fixed bed and wherein said butyrolactone is contacted by passing through said bed in a continuous manner.

11. The process of claim 10 wherein said butyrolactone is passed through said bed at a rate of between about 10 ml and about 40 ml per hour.

* * * * *